United States Patent [19]

Chantzis

[11] Patent Number: 4,691,702
[45] Date of Patent: Sep. 8, 1987

[54] ASPIRATING DEVICE

[75] Inventor: Constantin B. Chantzis, Glen Rock, N.J.

[73] Assignee: Becton, Dickinson and Company, Franklin Lakes, N.J.

[21] Appl. No.: 916,358

[22] Filed: Oct. 8, 1986

[51] Int. Cl.$^4$ ............................................. A61M 16/00
[52] U.S. Cl. ........................... 128/207.16; 604/902; 604/171; 604/163
[58] Field of Search ................. 128/200.26, 207.14, 128/207.15, 207.16; 604/902, 171, 172, 118, 163, 271

[56] References Cited

U.S. PATENT DOCUMENTS

| | | | |
|---|---|---|---|
| 3,319,628 | 5/1967 | Halligan | 128/276 |
| 3,991,762 | 11/1976 | Radford | 128/276 |
| 4,243,040 | 1/1981 | Beecher | 604/271 |
| 4,300,550 | 11/1981 | Gandi et al. | 128/207.18 |
| 4,324,262 | 4/1982 | Hall | 128/328 |
| 4,569,344 | 2/1986 | Palmer | 128/207.16 |

Primary Examiner—Henry J. Recla
Attorney, Agent, or Firm—John L. Voellmicke

[57] ABSTRACT

An aspirating device includes a flexible catheter having a proximal portion including a proximal end, a distal portion including a distal end and a passageway therethrough. The catheter is adapted for insertion into the trachea of a patient and includes at least one aperture in its distal portion for allowing fluid communication between the exterior of the catheter and the passageway. A patient housing includes a proximal first end having a first opening, a distal second end having a second opening and a side wall therebetween defining a cavity in the patient housing. The catheter is positioned in the first opening and capable of passing through the second opening. A flexible sleeve surrounds a portion of the catheter having a far end connected at the distal portion of the catheter and a near end connected to the housing so that as the catheter moves distally through the second opening the sleeve covers that portion of the catheter extending outwardly from the second opening between the second opening and the far end of the sleeve. The sleeve is positioned so that when the catheter is moved proximally with respect to the housing the catheter moves through the first opening while leaving the sleeve within the housing.

21 Claims, 7 Drawing Figures

ASPIRATING DEVICE

BACKGROUND OF THE INVENTION

1. Field of the Invention

The present invention relates to an aspirating device for removing undesirable secretions from a mammalian body and more particularly concerns as aspirating device for use in suctioning undesirable secretions from the trachea of a patient.

2. Description of Related Information

Various forms of respiratory therapy require the use of a ventilator which is a device which provides for the movement of gases into and out of the pulmonary system. Usually a ventilator is used in conjunction with some form of artificial airway or tube which is inserted into the patient's trachea through the mouth (endotracheal tube) or into the patient's trachea through an incision in the patient's neck (tracheostomy tube). The tracheostomy procedure is sometimes preferred because it bypasses and therefore avoids complication with portions of the upper airway.

Artificial airways are established for adequately supporting ventilation for an extended period of time. The artificial airway also prevents a potential danger to the patient by diminishing the patient's ability to cough and to voluntarily remove undesirable secretions from the trachea. Accordingly, the removal of the secretions from a patient having a temporary artificial airway, for example, during therapy involving a ventilator, is affected by aspiration or suctioning. Patients with a substantial amount of secretions require frequent aspiration or suctioning to remove secretions from the trachea.

A known and available suctioning device is a suction catheter as described in U.S. Pat. No. 3,319,628 to Halligan. The suction catheter, as taught by Halligan, is connected to a source of vacuum and is inserted through the artificial airway and into the trachea of the patient wherein the suction forces draw secretions into the catheter and out of the trachea and the artificial airway. Halligan teaches an improved catheter having means for manual regulation of the vacuum forces. In particular, Halligan teaches a suction catheter comprising a flexible catheter having an opening at its distal end and a rigid regulator at its proximal end. The regulator includes a bore which is aligned with the lumen of the catheter and a second bore which is perpendicular to the fluid path of the catheter in the first bore. A finger engaging piece is associated with the regulator and includes a concave surface adapted to recevie the finger of the user for occluding the secondary bore. The secondary bore acts as a bleed so that when it is not occluded, outside air enters the bore in the vacuum line and reduces the vacuum forces at the distal tip of the catheter to substantially zero while occluding the secondary bore with the finger terminates all bleed air and maximizes the vacuum forces at the tip of the catheter and partial occlusion will tend to provide vacuum forces between the two extremes. The catheter taught by Halligan provides an effective device for suctioning the trachea and other body passageways. These suction catheters are simple in structure, maneuverable, easy to regulate with respect to suction forces and disposable. The disposability is believed to be a desirable feature because bacteria encountered in the patient's trachea is deposited on the exterior of the catheter and under certain circumstances will continue to grow and multiply. Also, after removal of the catheter from the patient, other airborne bacteria may contact and grow on the catheter surface. Accordingly, reusing such an instrument is believed to be hazardous to the patient because it could introduce bacteria into the respiratory system and/or expose the user (doctor, respiratory therapist, nurse) to bacteria from the patient's trachea. A similarly structured suction and oxygenation catheter is taught by Gandi et al. in U.S. Pat. No. 4,300,550.

Bradford, in U.S. Pat. No. 3,991,762 teaches a resuable aspirating device for use with the patient ventilation apparatus. In one embodiment, Bradford teaches an aspirating device consisting of a catheter tube and a protective housing. The protective housing includes a patient coupling element slidably positioned so as to surround the catheter tube nearest the end thereof suitable for insertion into the trachea and a vacuum coupling element mounted adjacent to the end of the catheter remote from the end adapted to be inserted into the trachea and a protective envelope exending between the patient coupling element and the vacuum coupling element, formed of a flexible plastic material which distorts and compresses when the vacuum coupling element and the patient coupling element are moved relatively toward one another. The patient coupling element also includes a seal surrounding the catheter tube and adapted to help prevent fluid secretions located on the exterior surface of the catheter from being withdrawn, and an irrigation port suitable for connection to an irrigation source and in communication with the external surface of the catheter tube. Bradford teaches that the aspiration device should remain connected to the ventilation apparatus via the patient coupling element and that the same catheter can be reused many times by a single patient. Although the Bradford aspirating device appears to be more expensive to manufacture it may be an improvement, with respect to cost, if several aspirating procedures can be performed with the same device which remains continuously connected to the ventilator during the patient therapy. Also, the apparatus taught by Bradford, offers the advantage of being usable without disconnecting the ventilator so that it is not necessary to follow the procedure of pre-oxygenating the patient before using the suction catheter and a subsequent re-oxygenating step after use of the suction catheter. In addition, the respiratory therapist is not under the time pressure to perform the suctioning procedure in a minimal amount of time while the ventilator is disconnected.

Although the device taught by Bradford may provide some advantages over the prior art disposable suction catheters, it still has disadvantages. Most notably, the entire outer surface of the catheter which comes in contact with the secretions in the ventilator and in the patient's trachea is moved outwardly into the environment after each use, being protected only by the flexible cover. Although a seal is provided in the patient coupling element and irrigation may minimize the amount of secretion on the exterior of the catheter, it is believed that bacteria on the catheter surface is free to grow while the catheter is outside of the patient housing. Bradford has a further disadvantage in that any imperfection of destruction of the protective envelope may allow contamination of the environment and the respiratory therapist operating the catheter device. In addition, another disadvantage is that if the protective envelope is damaged or contains an imperfection, there is a possibility of infecting the patient with environmental bacteria which passes through the envelope and contaminates the catheter.

Palmer, in the U.S. Pat. No. 4,569,344 teaches an aspirating/ventilating apparatus similar to the apparatus taught by Bradford.

Catheters and catheter assemblies for use in suctioning of the trachea and other passages in a patient's body, for use alone or with a ventilator, both disposable and reusable, have been addressed by the prior art, as alluded to above. However, there is still a need for a simple, straight-forward, reliable, easily fabricated resuable aspirating device having reduced potential for contamination between suctioning procedures.

SUMMARY OF THE INVENTION

The aspirating device of the present invention, for use in removing undesirable secretions, includes a flexible catheter having a proximal portion including a proximal end, a distal portion including a distal end and a passageway therethrough. The catheter is adapted for insertion into the trachea of a patient and includes at least one aperture in its distal portion for allowing fluid communication between the exterior of the catheter and the passageway. A patient housing includes a proximal first end having a first opening, a distal second end having a second opening and a side wall therebetween defining a cavity in the patient housing. The catheter is positioned so that it passes through the first opening and is capable of passing through the second opening. A flexible sleeve surrounds a portion of the catheter. This sleeve includes a far end connected to the proximal portion of the catheter and a near end connected to the housing so that as the catheter is moved distally through the second opening of the housing, the sleeve covers that portion of the catheter extending outwardly from the second opening between the second opening and the far end of the sleeve. The sleeve is positioned so that when the catheter is moved proximally with respect to the housing and portions of the catheter move proximally through the first opening, the sleeve remains within the housing.

In the preferred embodiment of the present invention, an operable aspirating device for use in conjunction with the patient ventilation apparatus for removing undesirable secretions includes an elongate flexible catheter having a proximal portion including a proximal end, a distal portion including a distal end and a passageway therethrough. The catheter is adapted for insertion through the ventilation apparatus and into the trachea of a patient. The catheter includes at least one aperture in its distal portion for allowing fluid communication between the exterior of the catheter and the passageway. The patient housing includes a proximal first end having a first opening, a distal second end having a second opening and a side wall therebetween defining a cavity in the patient housing. The catheter is positioned within the first opening and capable of passing through the second opening. The housing includes means for connecting the housing to a patient ventilating apparatus so that the catheter may enter the patient ventilating apparatus through the second opening in the housing. A flexible sleeve surrounds a portion of the catheter. The sleeve includes a far end connected at the distal portion of the catheter and a near end connected to the housing, preferably at an interior surface of the cavity of the housing, so that as the catheter is moved distally through the second opening, the sleeve covers portions of the catheter extending outwardly from the second opening between the second opening and the far end of the sleeve. The sleeve is capable of contacting the patient's trachea and allows rotational movement of the catheter with respect to the housing. The sleeve is positioned so that when the catheter is moved proximally with respect to the housing the catheter moves along the first opening while leaving the sleeve within the housing. The housing also includes an irrigation port for allowing fluid communication between the exterior of the patient housing and the exterior of the sleeve for irrigation of the exterior of the sleeve. A vacuum coupling housing is connected to the proximal end of the catheter. The vacuum coupling housing is adapted for communication to a source of vacuum for establishing fluid communication between the source of vacuum and the passageway in the catheter.

In accordance with the principles of the present invention a number of advantages are achieved. Primarily, the present invention provides a simple, straight-forward, reliable, easily fabricated aspirating device which may be used in conjunction with a ventilation system on the same patient without disposal of the aspiration device. The instant invention also provides a unique structure which functions so that surfaces of the catheter and the flexible sleeve which contact the patient's traches do not pass through the proximal end of the housing, thereby reducing the potential for contamination of the catheter and infecting the personnel operating the ventilation and aspirating devices.

DETAILED DESCRIPTION

While this invention is satisfied by embodiments in many different forms, there is shown in the drawings and will herein be described in detail a preferred embodiment of the invention with the understanding that the present disclosure is to be considered as exemplary of the principles of the invention and is not intended to limit the invention to the embodiment illustrated. The scope of the invention will be measured by the appended claims and their equivalents.

Adverting to FIGS. 1-5, an operable aspirating device 20 for use in removing undesirable secretions includes an elongate flexible catheter 21 having a proximal portion 22, including a proximal end 23, a distal portion, a distal end 25 and a passageway 26 therethrough. For the purposes of the description of the present invention, the term "distal" is meant to refer to that end of the aspirating device which is furthest from the person holding the aspiration device, whereas the term "proximal" is meant to refer to the end of the aspirating device closest to the holder of the device.

The catheter is adapted for insertion through a portion of a ventilating apparatus, to be described in more detail hereinafter, and into the trachea of a patient. To facilitate insertion into the trachea, the distal end of the catheter should be formed so that, wherever possible, the edges are gently rounded to facilitate smooth insertion. One way to achieve this end is to provide a rounded, convexly-shaped closed end 27 on the catheter and an aperture 28 in distal end 25, in the catheter side wall, for allowing fluid communication between the exterior fo the catheter and passageway 26. It is within the purview of the instant invention to include catheters of a wide variety of lengths and diameters. A desirable catheter length is about 560 mm long having an outside diameter of approximately 4.7 mm. However, the choice of catheter length and diameter will be influenced by compatibility with other respiratory devices being used with the catheter and, more importantly, by accepted medical standards for the procedure being performed.

A patient housing 29 includes proximal first end 31 having a first opening 32 therein, a distal second end 33 having a second opening 34 therein, and a side wall 35 therebetween, defined a cavity 37 in the patient housing.

Catheter 21 passes through first opening 32 and, in this preferred embodiment is capable of passing through second opening 34. It is desirable to produce the catheter assembly so that distal end 23 of the catheter can be withdrawn into patient housing 29 so that the catheter does not project into the ventilator air passageway when it is not in use, and so that the catheter tip will be protected between uses and/or during shipping. However, this structure is merely preferred and not necessary and a functional aspirating device can be made where, even in the retracted position, catheter 21 protrudes through distal opening 34 of the housing.

Figure 5:
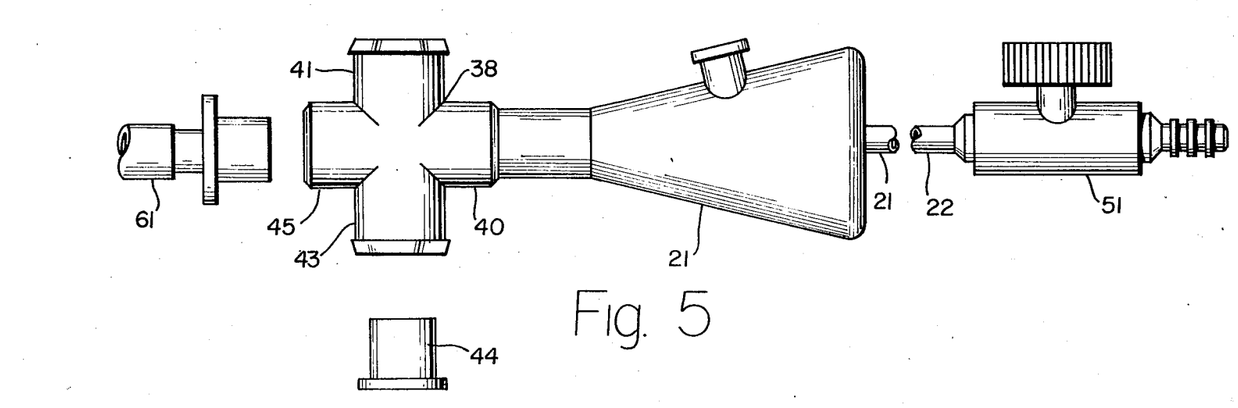
FIG. 5 is a side elevation exploded view of the aspirating device of the present invention illustrated with portions of a patient ventilating system.

Patient housing 29 includes a means for connecting the housing to a patient ventilating apparatus so that the catheter may enter the patient through the ventilating apparatus. As best illustrated in FIG. 5, cross-shaped connector 38 of a ventilating apparatus, which will be explained in more detail hereinafter, is capable of joining the aspirating device via a slight interference fit between the controlled outside diameter 39 of distal end 33 of the patient housing and the inside bore (not shown) of the cross-shaped ventilator connector at port 40. Port 41 of cross-shaped connector 38 is provided for communication with the portion of the ventilator apparatus which provides the desired gas mixture for patient respiration. Port 43, which is normally sealed by plug 44 is provided for communication with additional apparatus. Port 45 is adapted for connection to an endotracheal tube or a tracheostomy tube 61 having a distal end, (not shown) positioned in the trachea of a patient.

A flexible sleeve 46 surrounds a portion of the catheter. Sleeve 46 includes a far end 47 which is preferably connected to the catheter at distal portion 24. Sleeve 46 also includes a near end 49 which is preferably connected to an interior surface, such as surface 50, of cavity 37 in the housing. The flexible sleeve is attached to the catheter and to the housing so that as the catheter is moved distally through second opening 34 of the housing, the sleeve will cover that portion of the catheter extending outwardly from the second opening between the second opening and the position on the catheter where far end 47 of the sleeve is attached to catheter 21. Sleeve 46 is capable of contacting the patient's trachea when the catheter passes through a ventilation device. The sleeve is preferably constructed so that it will allow the angular rotation of the catheter with respect to the housing which is a desirable feature to facilitate suctioning especially where the catheter contains side holes and these side holes must be moved around the trachea to facilitate the suctioning procedure.

The interior of the housing and the sleeve are constructed to allow the catheter to be withdrawn from the patient's trachea and through the patient housing while the sleeve, which contacts the patient's trachea, remains within the housing and does not pass beyond proximal first end 31 of the housing. An important feature of the present invention is that the tip of the catheter and the portion of the sleeve which contacts the patients trachea can be withdrawn from the patient's trachea without any of the portions which contact the trachea leaving, or passing in a distal direction, past proximal first end 31 of the housing. This feature is believed to be a significant advantage over prior art devices having a protective envelope wherein the envelope is connected between a patient housing and the proximal end of the catheter. In these prior art devices the envelope is exposed during the time period between consecutive suctioning operations and may be damaged in a manner that will allow communication between the outside surface of the catheter which may contain bacteria from the patient's trachea and the environment so that there is a potential danger to the user from bacteria which could escape through the damaged envelope and potential danger to the patient from bacteria that may enter from the environment through the damaged envelope. The instant invention minimizes the above-recited potential for contamination by keeping all patient contacting surfaces of the device forward of or within the patient housing. Thus, the instant invention overcomes a major shortcoming of the prior art.

It is within the purview of the instant invention to include the proximal end of the catheter having a plain end, with the passageway running to the proximal end. In use, the proximal end of the catheter could be forced onto a tubing adapter of a regulatable vacuum source. It is also within the purview of the present invention to include a vacuum coupling means at the proximal portion to facilitate fluid communication between the passageway of the catheter and a source of vacuum. For example, a tubing fitting or vacuum coupling housing may be provided at the proximal end of the catheter.

In this preferred embodiment, vacuum coupling means includes vacuum coupling housing 51 connected to proximal end 23 of the catheter and tubing conector 52 which is adapted for insertion into a compatible flexible vacuum line or fitting (not shown). The suction forces may be regulated by any number of devices which can be provided in the vacuum system. Hovwer, it is preferred, but not necessary, that the vacuum coupling housing include a means for regulating vacuum forces within the catheter passageway. This vacuum control means can be structured along the lines of the teachings of U.S. Pat. No. 3,319,628 to Halligan. Essentially, the vacuum control means can include a vacuum control port (not shown) which provides for fluid communication between the vacuum line and the environment and, preferably, some mechanical means for fully occluding, partially occluding or allowing substantially full opening of the vacuum control port to the environment. The control means may comprise a screw-type needle valve or, preferably, a spring loaded, normally closed, valve which may be activated by pushing control knob 53 toward vacuum coupling housing 51 to open the vacuum control port to the environment and to reduce the suction forces in the catheter. It will be apparent to one skilled in the art that numerous methods may be used to join a catheter and a vacuum coupling housing. Such methods include the use interference fits between the inside diameter of the catheter and a tubing connector on the housing, adhesives, ultrasonic welding, internally positioned metal grommets or tubes which are large enough to provide considerable anchoring force between the catheter and the housing, and the like.

The preferred embodiment of the instant invention includes an irrigation port 56 in housing 29. The irrigation port is provided for allowing fluid communication between the exterior of the patient housing and the exterior of the flexible sleeve so that irrigating fluid can be externally provided for flushing over the exterior of the flexible sleeve to help remove undesirable secretions on the sleeve which have accumulated during a suctioning procedure. Ideally, these fluids will wash the secretions toward distal end 25 of the catheter wherein they will be drawn through aperture 28 and through the passageway of the catheter, toward the vacuum source. Irrigation port 56 is normally occluded by removable plug 57, which can be removed to allow irrigation and replaced after the irrigation procedure. It is also within the purview of the instant invention to provide an irrigation port which is occluded by a fixed pierceable septum wherein irrigating fluid can be provided by injection with a hypodermic syringe having a sharpened needle for piercing the septum.

Figure 1:
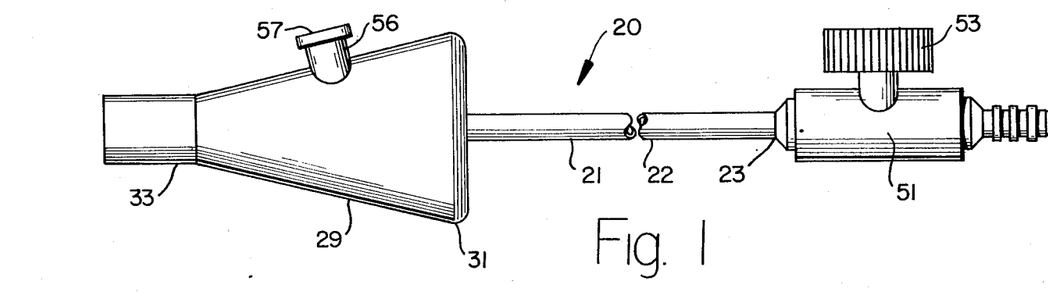
FIG. 1 is a side elevation view of the preferred aspirating device of the present invention.
Figure 2:
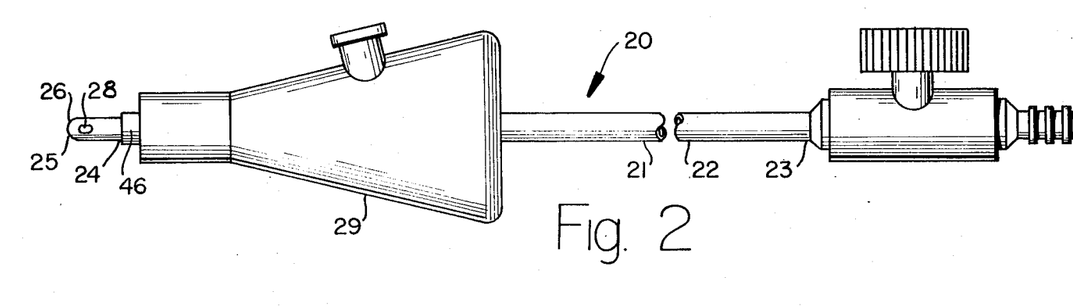
FIG. 2 is another side elevation view of the aspirating device of the present invention illustrating the catheter in a partially advanced position so that the catheter tip protrudes from the patient housing.
Figure 3:
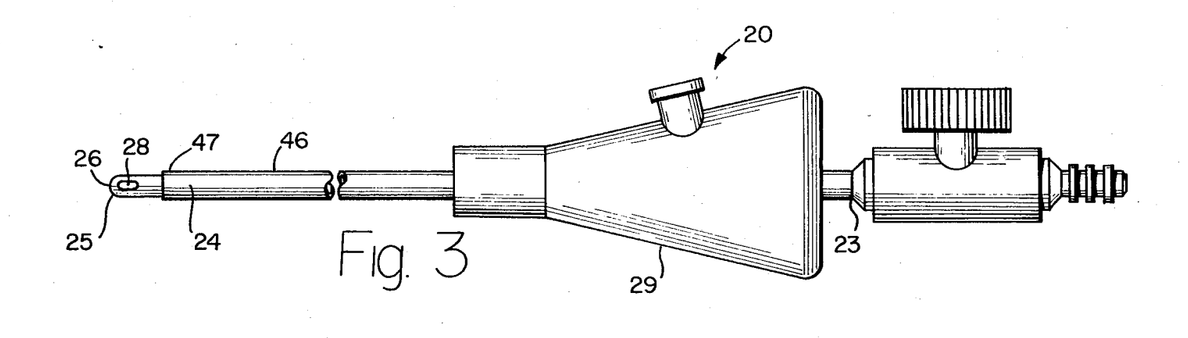
FIG. 3 is another side elevation view of the aspirating device of the present invention illustrating the catheter in a fully extended position with respect to the patient housing.
Figure 4:
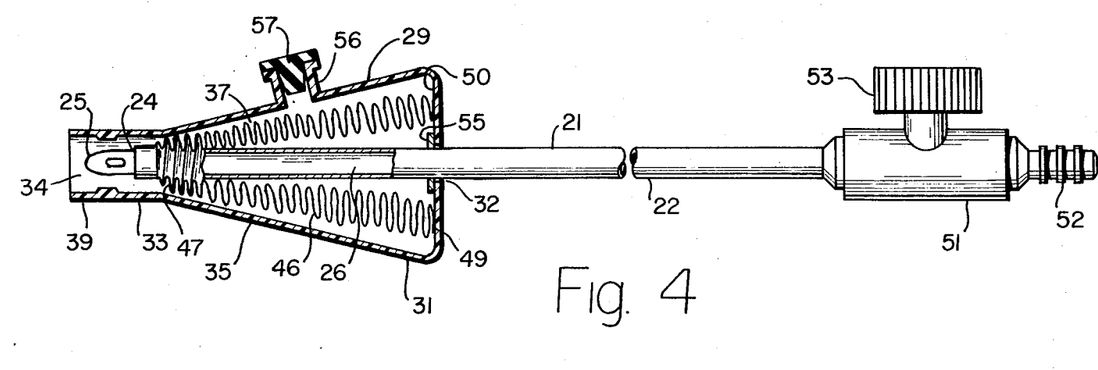
FIG. 4 is a partially cross-sectioned side elevation view of the aspirating device of the present invention illustrating the internal structure of the patient housing.

If, as will be explained in more detail hereinafter, a porous material is chosen for the sleeve or for other reasons, it may be desirable to provide seal means, such as seal 55, illustrated in FIG. 4. The seal is provided for restricting gas flow between the interior of patient housing 29 and the environment, through first opening 32 and outside of the catheter, to minimize the possible effect on ventilator performance by the passage of gases through the sleeve and the first opening. It is desirable to use a sleeve made of polymeric, preferably flexible, material which is attached to the housing, around the first opening, using adhesive, ultrasonic welding, mechanical joining or other suitable means. It is also within the purview of the instant invention to include a seal integrally formed with the housing. It is also desirable, but not necessary, for the seal to contact the catheter, providing a slidable engagement around the periphery of the catheter.

Referring now to FIGS. 1-6, in use, the aspirating device of the instant invention can be attached to a patient ventilation apparatus which includes a source of pressurized oxygen 58 delivering the oxygen through conduit 59 to port 41 of the cross-shaped connector 38 which is connected to, for example, a tracheostomy tube 61 which is partially positioned in the patient's trachea. From time to time during the ventilation procedure it will be necesary to remove undesirable secretions from the patient's trachea. The aspiration device of the instant invention may be used in performing an aspiration or suctioning procedure to remove the secretions. Because the aspiration device is connected to the ventilator via connector 38 it is not necessary to disconnect the ventilator from the patient. To peform an aspirating procedure the nurse may activate the source of the vacuum V and provide sterile irrigating liquid through irrigation port 56 before advancing the catheter into the patient's trachea. The catheter may be advanced by holding the patient housing in one hand and advancing the catheter, possibly by holding the vacuum coupling housing in the other hand. The catheter tip will advance through second opening 34 through the ports 40 and 45 in the cross-shaped connector and through tracheostomy tube 61. The user can regulator the vacuum through the means provided, for example, the vacuum control means controlled by vacuum control knob 53 and manipulate simultaneously the cannula by moving inwardly and outwardly or rotationally to remove the secretions. At the end of the procedure, it may be desirable to inject more sterile irrigating fluid through the irrigation port while withdrawing the catheter in a proximal direction out of the ventilator system. The catheter may now remain in place until the next aspiration procedure. It should be noted again that in the rest position none of the surfaces which contact the patient's trachea leave the patient housing so that portions of the aspirating device positioned proximally from the patient housing are the external surfaces of portions which have not been in contact with the secretions in the patient's trachea.

Figures 6, 7:
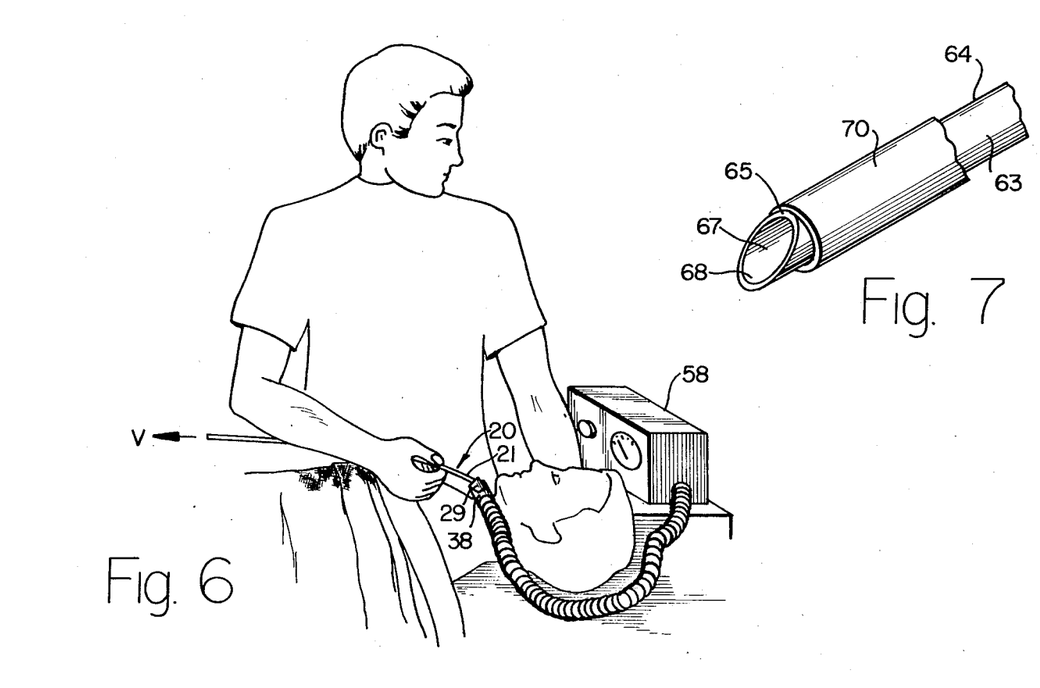
FIG. 6 is a perspective view illustrating the aspirating device of the present invention being used in patient therapy.
FIG. 7 is a perspective view of an alternative structure for the distal portion of the catheter in the aspirating device of the present invention.

Referring to FIG. 7, an alternative embodiment of the present aspirating device, substantially identical to the device described in FIGS. 1-6, except that a catheter 63 having distal portion 64 including distal end 65 and passageway 67 includes an aperture 68 at the distal end to facilitate the suctioning procedure. A flexible sleeve 70 is attached at the distal portion of the catheter.

A wide variety of flexible materials are suitable for fabricating the flexible sleeve. Such materials include natural rubber, synthetic rubber and thermoplastic materials. The choice of a sleeve material may be influenced by the method used for sealing the sleeve to the catheter and to the housing, for example, heat sealing, adhesives, ultrasonic welding, mechanical joining and the like. It is preferred that the sleeve be constructed of a thin membrane-like material having a thickness of between about 0.003 inch and 0.010 inch (0.076 mm and 0.25 mm) so that the sleeve can be collapsed into a relatively small housing while acting as a barrier to the transmission of bacteria and liquid accumulated during the suctioning procedure. A suitable material is manufactured by W. L. Gore and Associates, Inc., of Elkton, Md. known as GORETEX® membranes and laminates. Such membranes are available in materials such as polytetrafluoroethylene, polyester, polyvinylchloride, polypropylene and polyethylene. These membranes are available in various pore ratings. It is preferred that the membrane has a maximum pore rating of 0.5 micron so that it will act as an effective barrier for particles greater than 0.5 micron which include bacteria. These membranes, however, are an effective barrier against the passage of liquid. These membranes are also available with porous backing sheets which are laminated to the membrane for providing a stronger more stable structure preferably having a thickness of between about 0.006 inch and 0.015 inch (0.15 mm and 0.38 mm). It is preferred that a polytetrafluoroethylene membrane with laminated backing sheet be used for forming the flexible sleeve of the instant invention. The membrane and/or laminate structure can be formed into a cylinder or frusto-conically shaped cylinder by heat sealing along a longitudinal seam and then the sleeve is heat sealed or adhesive bound or ultrasonically welded to the catheter on one end and to the patient housing on the other end. The sleeve may also be made of extruded polymeric material.

A wide variety of flexible materials are suitable for forming the catheter with thermoplastic materials such as polyvinylchoride and polyethylene being preferred. A wide variety of rigid materials can be used for forming the patient housing and the vacuum coupling housing with rigid thermoplastic materials such as polystyrene, polyethylene, polyvinylchloride being preferred. It is also preferred that all the elements of the aspirating device of the instant invention be sterile when used. Accordingly, material should be selected for compatibility with the sterilization process being used.

Thus, it can be seen that the present invention provides a simple, straight-foward, reliable, easily fabricated aspirating device which may be used in conjunction with a ventilation system and allows performance of multiple aspirating procedures on the same patient without disposal of the aspirating device. The instant invention also provides a unique structure which functions so that the surfaces of the catheter and the flexible sleeve which contact the patient's trachea do not pass through the proximal end of the housing, thereby reducing the potential for contamination of the catheter and the infecting personnel operating the ventilation and aspirating devices.

What is claimed is:

1. An operable aspirating device for use in conjunction with a patient ventilation apparatus for removing undesirable secretions comprising:
    an elongate flexible catheter having a proximal portion including a proximal end, a distal portion including a distal end and a passageway therethrough, said catheter being adapted for insertion through said ventilating apparatus and into the trachea of a patient, said catheter having at least one aperture in said distal portion for allowing fluid communication between the exterior of said catheter and said passageway;
    a patient housing including a proximal first end having a first opening, a distal second end having a second opening and a side wall therebetween defining a cavity in said patient housing, said catheter passing through said first opening and capable of passing through said second opening, said housing including means for connecting said housing to a patient ventilation apparatus so that said catheter may enter said patient ventilation apparatus through said second opening; and
    a flexible sleeve surrounding a portion of said catheter having a far end connected at said distal portion of said catheter and a near end connected to said housing so that as said catheter is moved distally through said second opening said sleeve covers the portion of said catheter extending outwardly from said second opening between said second opening and said far end of said sleeve, said sleeve being capable of contacting the patient's trachea, said sleeve allowing rotational movement of said elongate catheter with respect to said housing, said sleeve being positioned so that when said catheter is moved proximally with respect to said housing said catheter moves through said first opening while leaving said sleeve within said housing.

2. The aspirating device of claim 1 further including vacuum coupling means at said proximal portion of said catheter for facilitating fluid communication between said passageway and a source of vacuum.

3. The aspirating device of claim 2 wherein said vacuum coupling means includes a vacuum coupling housing connected to said proximal end of said catheter and adapted for connection to a source of vacuum for establishing fluid communication between said source of vacuum and said passageway.

4. The aspirating device of claim 3 wherein said vacuum coupling housing includes a vacuum control port for establishing fluid communication between the exterior of said vacuum control housing and said passageway.

5. The aspirating device of claim 4 further including valve means for occluding said vacuum control port for regulating the vacuum forces in said passageway.

6. The aspirating device of claim 1 wherein said housing includes an irrigation port for allowing fluid communication between the exterior of said patient housing and the exterior of said sleeve for irrigation of the exterior of said sleeve.

7. The aspirating device of claim 1 wherein said distal end of said catheter is closed.

8. The aspirating device of claim 1 wherein said sleeve is made from materials selected from the group consisting of natural rubber, synthetic rubber and thermoplastic materials.

9. The aspirating device of claim 1 wherein said sleeve includes a thin membrane.

10. The aspirating device of claim 9 wherein said membrane is made of polymeric material selected from the group consisting of polytetrafluoroethylene, polyester, polyvinylchloride, polypropylene and polyethylene.

11. The aspirating device of claim 9 wherein said membrane is made of porous material having a maximum pore rating of 0.5 micron for serving as a substantial barrier to particles about 0.5 micron and larger, said membrane also serving as a liquid barrier.

12. The aspirating device of claim 11 further including a thin porous backing sheet laminated to said membrane to provide stabliity to the composite structure of said membrane and said backing sheet.

13. The aspirating device of claim 11 further including seal means for restricting gas flow between said cavity in said housing and the environment through said first opening.

14. The aspirating device of claim 13 wherein said seal means includes a seal connected to said housing at said first opening and surrounding said catheter.

15. The aspirating device of claim 1 when said catheter is made from thermoplastic material selected from the group of polyvinylchloride and polyethylene.

16. An operable aspirating device for use in removing undesirable secretions comprising:
    a flexible catheter having a proximal portion including a proximal end, a distal portion including a distal end and a passageway therethrough, said catheter being adapted for insertion into the trachea of a patient, said catheter having at least one aperture in said distal portion for allowing fluid communication between the exterior of said catheter and said passageway;

a patient housing including a proximal first end having a first opening, a distal second end having a second opening and a side wall therebetween defining a cavity in said patient housing, said catheter passing through said first opening and capable of passing through said second opening said housing including means for connecting said housing to a patient ventilation apparatus so that said catheter may enter said patient ventilation apparatus through said second opening; and a flexible sleeve surrounding a portion of said catheter having a far end connected at said distal portion of said catheter and a near end connected to said housing so that as said catheter is moved distally through said second opening said sleeve covers the portion of said catheter extending outwardly from said second opening between said second opening and said far end of said sleeve, said sleeve being positioned so that when said catheter is moved proximally with respect to said housing said catheter moves through said first opening while leaving said sleeve within said housing.

17. An operable aspirating device for use in conjunction with a patient ventilation apparatus for removing undesirable secretions comprising:

an elongate flexible catheter having a proximal portion including a proximal end, a distal portion including a distal end and a passageway therethrough, said catheter being adapted for insertion through said ventilation apparatus and into the trachea of a patient, said catheter having at least one aperture in said distal portion for allowing fluid communication between the exterior of said catheter and said passageway;

a patient housing including a proximal first end having a first opening, a distal second end having a second opening and a side wall therebetween defining a cavity in said patient housing, said catheter passing through said first opening and capable of passing through said second opening, said housing including means for connecting said housing to a patient ventilation apparatus so that said catheter may enter said patient ventilation apparatus through said second opening;

a flexible sleeve surrounding a portion of said catheter having a far end connected at said distal portion of said catheter and a near end connected to said housing so that as said catheter is moved distally through said second opening said sleeve covers the portion of said catheter extending outwardly from said second opening between said second opening and said far end of said sleeve, said sleeve being capable of contacting the patient's trachea, said sleeve allowing rotational movement of said elongate catheter with respect to said housing, said sleeve being positioned so that when said catheter is moved proximally with respect to said housing said catheter moves through said first opening while leaving said sleeve within said housing;

said housing including an irrigation port allowing fluid communication between the exterior of said patient housing and the exterior of said sleeve for irrigation of the exterior of said sleeve; and a vacuum coupling housing connected to said proximal end of said catheter adapted for communication to a source of vacuum for establishing fluid communication between said source of vacuum and said passageway.

18. The aspirating device of claim 17 wherein said vacuum coupling housing includes a vacuum control port for establishing fluid communication between the exterior of said vacuum control housing and said passageway, and valve means for occluding said vacuum control port for regulating the vacuum forces in said passageway.

19. The aspirating device of claim 17 wherein said sleeve includes a thin membrane.

20. The aspirating device of claim 19 wherein said membrane is made of porous material having a maximum pore rating of 0.5 micron for serving as a substantial barrier to particles about 0.5 micron and larger, said membrane also serving as a liquid barrier.

21. The aspirating device of claim 20 further including seal means for restricting gas flow between said cavity in said housing and the environment through said first opening.

* * * * *